United States Patent [19]

Sasajima et al.

[11] 4,009,173
[45] Feb. 22, 1977

[54] BUTYROPHENONE DERIVATIVES

[75] Inventors: Kikuo Sasajima, Toyonaka; Masaru Nakao, Osaka; Isamu Maruyama, Minoo; Keiichi Ono, Osaka; Shigenari Katayama; Shigeho Inaba, both of Takarazuka; Hisao Yamamoto, Nishinomiya, all of Japan

[73] Assignee: Sumitomo Chemical Company, Limited, Japan

[22] Filed: Sept. 29, 1975

[21] Appl. No.: 617,730

Related U.S. Application Data

[63] Continuation of Ser. No. 368,909, June 11, 1973, abandoned.

[30] Foreign Application Priority Data

June 12, 1972   Japan .............................. 47-58789

[52] U.S. Cl. .................... 260/293.64; 260/293.77; 260/293.71; 260/293.79; 424/267; 260/247.2 A; 260/247.5 G; 260/293.61
[51] Int. Cl.[2] ...................................... C07D 403/04
[58] Field of Search ................ 260/293.64, 293.77, 260/293.79; 424/267

[56] References Cited

UNITED STATES PATENTS

| | | | |
|---|---|---|---|
| 3,041,344 | 6/1962 | Janssen | 260/293.64 |
| 3,097,209 | 7/1963 | Janssen | 260/293.64 |
| 3,799,932 | 3/1974 | Yamamoto et al. | 260/293.79 |
| 3,850,935 | 11/1974 | Nakao et al. | 260/293.8 |
| 3,907,812 | 9/1975 | Yamamoto et al. | 260/293.79 |

Primary Examiner—Norma S. Milestone
Attorney, Agent, or Firm—Craig & Antonelli

[57] ABSTRACT

Novel butyrophenone derivatives of the formula:

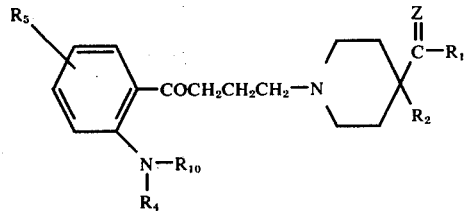

wherein $R_1$ represents a hydroxyl group or

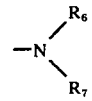

(wherein $R_6$ and $R_7$ are each a hydrogen atom or a lower alkyl group or, when taken together with the adjacent nitrogen atom, may form a heterocyclic group), $R_2$ represents an optionally substituted phenyl group or

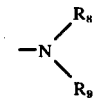

(wherein $R_8$ and $R_9$ are each a hydrogen atom or a lower alkyl group or, when taken together with the adjacent nitrogen atom, may form a heterocyclic group), $R_4$ represents a hydrogen atom, a lower alkyl group or an optionally substituted phenyl group, $R_5$ represents a hydrogen atom, a halogen atom, a lower alkyl group, a lower alkoxy group or a trifluoromethyl group, $R_{10}$ represents a hydrogen atom or an acyl group represented by $R_3CO-$ (wherein $R_3$ is a hydrogen atom, a lower alkyl group or an optionally substituted phenyl group) and Z represents two hydrogen atoms or an oxygen atom, provided that when Z is an oxygen atom and $R_1$ is

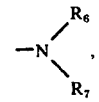

$R_{10}$ can not be a hydrogen atom, and their acid addition salts, which are useful as central and autonomic nervous system depressants.

2 Claims, No Drawings

BUTYROPHENONE DERIVATIVES

This is a continuation, of application Ser. No. 368,909 filed June 11, 1973, now abandoned.

This invention relates to novel butyrophenone derivatives and their salts, and production thereof. More particularly, the invention relates to novel butyrophenone derivatives represented by the formula:

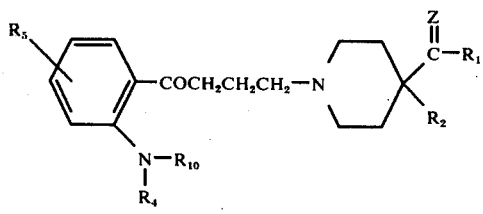
(I)

wherein $R_1$ represents a hydroxyl group or

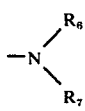

(wherein $R_6$ and $R_7$ are each of hydrogen atom or a lower alkyl group or, when taken together with the adjacent nitrogen atom, may form a heterocyclic group), $R_2$ represents an optionally substituted phenyl group or

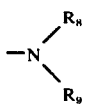

(wherein $R_8$ and $R_9$ are each a hydrogen atom or a lower alkyl group or, when taken together with the adjacent nitrogen atom, may form a heterocyclic group), $R_4$ represents a hydrogen atom, a lower alkyl group or an optionally substituted phenyl group, $R_5$ represents a hydrogen atom, a halogen atom, a lower alkyl group, a lower alkoxy group or a trifluoromethyl group, $R_{10}$ represents a hydrogen atom or an acyl group represented by $R_3CO$- (wherein $R_3$ is a hydrogen atom, a lower alkyl group or an optionally substituted phenyl group) and Z represents two hydrogen atoms or an oxygen atom, provided that when Z is an oxygen atom and $R_1$ is

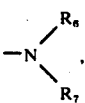

$R_{10}$ can not be a hydrogen atom, and their acid addition salts, and to a process for producing them.

In the above significances, a lower alkyl group includes methyl, ethyl, n-propyl, isopropyl, n-butyl and sec.-butyl; a lower alkoxy group includes methoxy, ethoxy, n-propoxy, isopropoxy, n-butyoxy and t-butoxy; a halogen atom includes fluorine, chlorine, bromine and iodine; and an optionally substituted phenyl group includes phenyl substituted or not with one or two substituents selected from the group consisting of halogen, hydroxyl, lower alkyl, lower alkoxy and trifluoromethyl; and a heterocyclic group which may be formed by

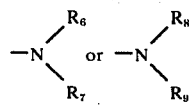

includes pyrrolidino, piperidino, hexamethyleneimino and morpholino.

These butyrophenone derivatives [I] have various depressing activities on the central and autonomic nervous systems and are useful as neuroleptics, traquilizers, sedatives, analgesics and/or antihypertensives. They are also useful as intermediates in the production of neuroleptic, sedative or antiinflammatory agents.

Accordingly, a main object of the present invention is to provide the novel butyrophenone derivatives [I]. Another object of this invention is to provide the butyrophenone derivatives [I] useful as central and autonomic nervous system depressants. A further object of the invention is to provide an advantageous process for producing the butyrophenone derivatives [I]. Other objects of this invention will be apparent from the following descriptions.

According to the present invention, the butyrophenone derivatives [I] and their salts are prepared by contacting an indole compound represented by the formula:

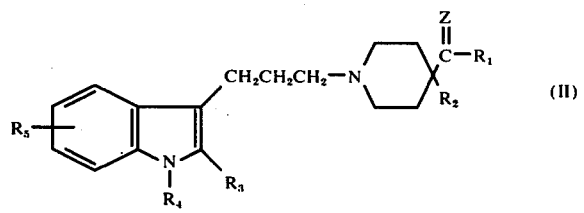
(II)

wherein $R_1$, $R_2$, $R_3$, $R_4$, $R_5$ and Z are each as defined above or its acid addition salt with an oxidizing agent to give an acylated amine compound of the formula:

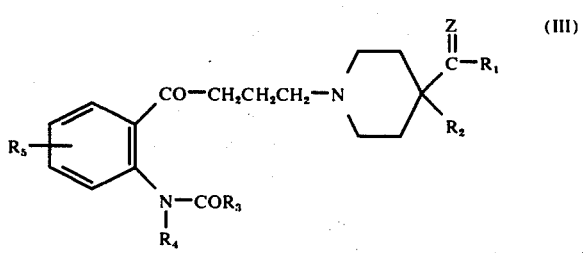
(III)

wherein $R_1$, $R_2$, $R_3$, $R_4$, $R_5$ and Z are each as defined above and, if necessary, hydrolyzing the latter to give an amine compound of the formula:

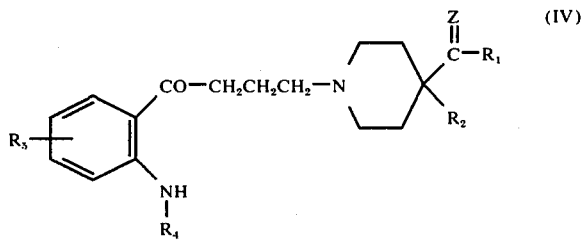 (IV)

wherein $R_1$, $R_2$, $R_4$, $R_5$ and Z are each as defined above; optionally followed by treatment with an acid.

As the oxidizing agent, there may be exemplified ozone, hydrogen peroxide, peracids (e.g. performic acid, peracetic acid, perbenzoic acid), chromic acid or potassium permanganate, although these are not limitative. The oxidizing agent is used in a stoichiometric amount or more.

The reaction is preferably effected in the presence of a solvent (e.g. water, acetone, formic acid, acetic acid, chloroform, methylene dichloride, carbon tetrachloride, ethyl acetate, benzene, pyridine, dimethylformamide, sulfuric acid). The choice of solvent depends on the oxidizing agent employed. In general, the reaction proceeds readily at room temperature. Since, however, the temperature varies depending on the oxidizing agent as employed, it may be higher or lower as necessary to effect the desired control of the reaction.

Chromic acid or ozone is a preferably oxidizing agent. When the reaction is performed with chromic acid in the presence of acetic acid, the chromic acid may be preferably employed in 2 to 10 times of the equimolar amount at room temperature. The reaction terminates within, in genreal, about 24 hours. When ozone is used, the reaction is favorably carried out by bubbling ozonized oxygen into a solution or suspension of the indole compound [II] or its salt in a solvent such as formic acid, acetic acid or carbon tetrachloride at room temperature while stirring.

The thus produced acylated amine compound [III] can be easily separated from the reaction mixture by extraction. If desired, the separated product may be further purified by a conventional procedure such as recrystallization or salt formation.

When necessary, the acylated amine compound [III] is deacylated to the corresponding amine compound [IV] by treating under an acidic or alkaline condition according to a conventional method for hydrolysis.

Examples of the butyrophenone derivatives [I], i.e. the acylated amine compound [III] and the amine compound [IV], obtained as above are as follows:

γ,  -(4′-Piperidino-4′-carbamoylpiperidino)-2-acetamino-4-fluorobutyrophenone;

γ-(4′-Piperidino-4′-aminomethylpiperidino)-2-acetamino-4-fluorobutyrophenone;

γ-(4′-Piperidino-4′-aminomethylpiperidino)-2-amino-4-fluorobutyrophenone;

γ-(4′-Piperidino-4′-carboxypiperidino)-2-amino-4-fluorobutyrophenone;

γ-(4′-m-Methylphenyl-4′-pyrrolidinocarbonyl-piperidino)-2-acetamino-4-fluorobutyrophenone;

γ-(4′m-Methylphenyl-4′-pyrrolidinomethyl-piperidino)-2-acetamino-4-fluorobutyrophenone;

γ-(4′-m-Methylphenyl-4′-pyrrolidinomethyl-piperidino)-2-amino-4-fluorobutyrophenone;

γ-(4′-m-Methylphenyl-b  4′-carboxypiperidino)-2-amino-4-fluorobutyrophenone;

γ-(4′-p-Chlorophenyl-4′-dimethylaminocarbonyliperidino)-2-acetamino-4-fluorobutyrophenone;

γ-(4′-p-Chlorophenyl-4′-dimethylaminomethyl-piperidino)-2-acetamino-4-fluorobutyrophenone;

γ-(4′-p-Chlorophenyl-4′-dimethylaminomethyl-piperidino)-2-amino-4-fluorobutyrophenone;

γ-(4′-p-Chlorophenyl-4′-carboxypiperidino)-2-amino-4-fluorobutyrophenone;

γ-(4′-Piperidino-4′-carbamoylpiperidino)-2-benzoylamino-4-fluorobutyrophenone;

γ-(4′-Piperidino-4′-carbamoylpiperidino)-2-ethylacetamino-4-fluorobutyrophenone;

γ-(4′-Piperidino-4′-carbamoylpiperidino)-2-phenylaacetamino-4-fluorobutyrophenone;

γ-(4′-Piperidino-4′-aminomethylpiperidino)-2-ethylamino-4-fluorobutyrophenone;

γ-(4′-Piperidino-4′-aminomethylpiperidino)-2-methylamino-4-fluorobutyrophenone;

γ-(4′-Piperidino-4′-aminomethylpiperidino)-2-phenylamino-4-fluorobutyrophenone;

γ-(4′-m-Methylphenyl-4′-piperidinocarbonyl-piperidino)-2-acetamino-4-fluorobutyrophenone;

γ-(4′-m-Methylphenyl-4′-morpholinocarbonyl-piperidino)-2-acetamino-4-fluorobutyrophenone;

γ-(4′-Pyrrolidino-4′-carbamoylpiperidino)-2-acetamino-4-fluorobutyrophenone;

γ-(4′-Morpholino-4′-carbamoylpiperidino)-2-acetamino-4-fluorobutyrophenone;

γ-(4′-m-Methylphenyl-4′-piperidinomethyl-piperidino)-2-acetamino-4-fluorobutyrophenone;

γ-(4′-m-Methylphenyl-4′-piperidinomethyl-piperidino)-2-amino-4-fluorobutyrophenone;

γ-(4′-m-Methylphenyl-4′-morpholinomethyl-piperidino)-2-acetamino-4-fluorobutyrophenone;

γ-(4′-m-Methylphenyl-4′-morpholinomethyl-piperidino)-2-amino-4-fluorobutyrophenone;

γ-(4′-Pyrrolidino-4′-aminomethylpiperidino)-2-acetamino-4-fluorobutyrophenone;

γ-(4′-Pyrrolidino-4′-aminomethylpiperidino)-2-amino-4-fluorobutyrophenone;

γ-(4′Morpholino-4′-aminomethylpiperidino)-2-acetamino-4-fluorobutyrophenone;

γ-(4′-Morpholino-4′-aminomethylpiperidino)-2-amino-4-fluorobutyrophenone, etc.

These butyrophenone derivatives [I] can be converted into their acid addition salts by treatment with acids such as hydrochloric acid, sulfuric acid, phosphoric acid, hydrobromic acid, thiocyanic acid, acetic acid, propionic acid, oxalic acid, citric acid, malic acid tartaric acid, fumaric acid, maleic acid, succinic acid, glycolic acid, benzoic acid, cinnamic acid p-aminosalicylic acid, salicylic acid, metasulfonic acid, ascorbic acid and the like.

The indole compound [II] used as the starting material can be prepared, for example, as shown in the following scheme:

(A) 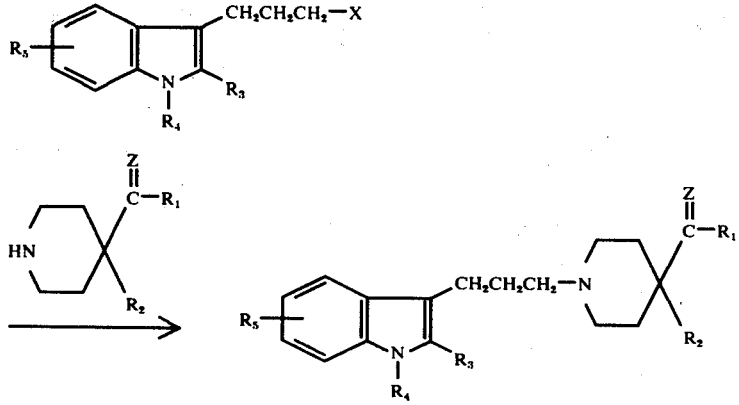

(B) 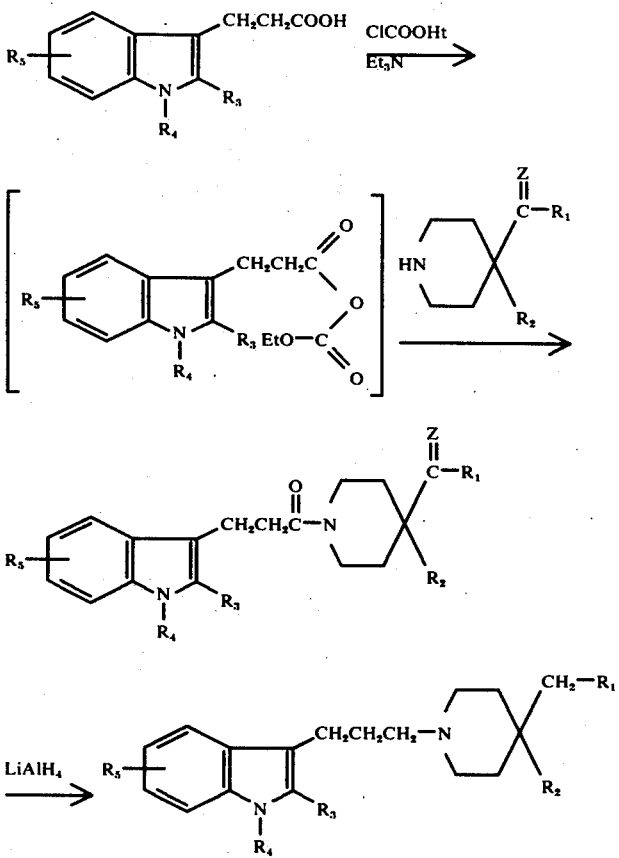

wherein $R_1$, $R_2$, $R_3$, $R_4$, $R_5$ and Z are each as defined above, X represents a halogen atom or an arylsulfonyloxy group.

The animal test revealed that the butyrophenone derivatives [I] have various depressing activities on the central and autonomic nervous systems. They exhibit beneficial pharmacological activites such as neuroleptic, tranquilizing, sedative, analgesic and/or antihypertensive activities.

Each of these compounds may be brought into a form suitable for administration according to a method known per se. For the preparation of pharmaceutical compositions, they may be mixed with carriers, diluents, lubricants, fillers and/or binders, sometimes together with stabilizers and emulsifying agents. The resulting mixture may be processed in a usual manner to tablets, capsules, pills, ampouls and the like.

Following examples are given to illustrate the present invention more precisely, but it is not intended to limit the present invention to these examples.

EXAMPLE 1

Five grams of 2-methyl-3[γ-(4'-piperidino-4'-carbamoylpiperidino)propyl]-61-fluoroindole hydrochloride were dissolved in 140 ml of acetic acid. While 2 – 3 % ozonized oxygen was bubbled into the solution at 10° to 20° C under cooling with ice-water, the reaction mixture gradually became red and the color turned pale with time. The reaction mixture was made alkaline by addition of 10 % aqueous sodium hydroxide solution and extracted with ethyl acetate. The ethyl acetate was evaporated from the extract under reduced pressure to obtain an oily viscous residue. The residue was treated with ethanolic hydrochloric acid to give γ-

(4'piperidino-4'-carbamoylpiperidino)-2-acetamino-4-fluorobutyrophenone hydrochloride. M.P. 233° – 238° C (decomp.).

EXAMPLE 2

As in Example 1, 2-methyl-3-[γ-(4'-piperidino-4'aminomethylpiperidino)propyl]-6-fluoroindole was oxidized to give γ-(4'-piperidino-4'-aminomethylpiperidino)-2-acetamino-4-fluorobutyrophenone hydrochloride. M.P. 290° C (decomp.).

What is claimed is:
1. γ-(4'-piperidino-4'-carbamoylpipridino)-2-acetamino-4-fluorobutyrophenone hydrochloride.
2. γ-(4'-piperidino-4'-aminomethylpiperidino)-2-acetamino-4-fluorobutyrophenone hydrochloride.

* * * * *